United States Patent [19]
Kuwata

[11] Patent Number: 5,209,566
[45] Date of Patent: May 11, 1993

[54] DYNAMIC THERMOMECHANICAL ANALYZER

[75] Inventor: Hiroji Kuwata, Kyoto, Japan
[73] Assignee: Shimadzu Corporation, Kyoto, Japan
[21] Appl. No.: 855,557
[22] Filed: Mar. 23, 1992

[30] Foreign Application Priority Data

Mar. 28, 1991 [JP] Japan ............... 3-64316

[51] Int. Cl.⁵ ............................ G01N 25/12
[52] U.S. Cl. ......................... 374/16; 374/17; 374/22
[58] Field of Search ............ 374/16, 17, 19, 22, 374/23, 25, 26

[56] References Cited

U.S. PATENT DOCUMENTS

| | | | |
|---|---|---|---|
| 3,201,970 | 8/1965 | Beaugh et al. | 374/23 |
| 3,202,602 | 8/1965 | Beaugh et al. | 374/23 X |
| 3,248,928 | 5/1966 | Conklin et al. | 374/19 |
| 3,498,104 | 3/1970 | Kerkvoort et al. | 374/23 |
| 4,804,274 | 2/1989 | Green | 374/25 X |

FOREIGN PATENT DOCUMENTS 1498698  7/1969  Fed. Rep. of Germany ........ 374/22

Primary Examiner—Daniel M. Yasich
Attorney, Agent, or Firm—Oliff & Berridge

[57] ABSTRACT

A testing apparatus (dynamic thermomechanical analyzer) for analyzing a change of the state of a sample from a fluid state to a solid state. The dynamic thermomechanical analyzer includes: a) a vessel in which the sample is set; b) a spring standing in the vessel; the top of the spring rising above the surface of the sample; c) an oscillator for oscillating the spring via a push rod with a constant amplitude of force; and d) a displacement detector for detecting the displacement of the spring or the push rod. When the spring is oscillated at a constant amplitude of force, the amplitude ΔL of the displacement of the push rod decreases as the initially fluid sample solidifies.

10 Claims, 3 Drawing Sheets

DYNAMIC THERMOMECHANICAL ANALYZER

The present invention relates to a testing apparatus for analyzing change of the state of a sample from fluid (that is, liquid or gel) to solid.

BACKGROUND OF THE INVENTION

Conditions or parameters for a change of state of a sample, such as the time needed for a two-ingredient type adhesive to solidify or the temperature for a gel sample to solidify, have been measured by differential thermal analyzers, which measures change in the specific heat of the sample. When the change in the specific heat of the sample is small or the change of the state is very slow in relation to the change in the time or temperature, however, the differential thermal analyzer is difficult to use.

When an adhesive is tested, it should include a test of solidifying characteristics under application of force since adhesives are often used under such conditions. Mere thermal analyzers are inadequate for such tests.

SUMMARY OF THE INVENTION

The apparatus of the present invention is the testing apparatus that can analyze the change of the state of a sample from fluid to solid even if the change is small and slow.

According to the present invention, the testing apparatus includes:

a) a vessel in which the sample is set;

b) a spring standing in the vessel, the top of the spring rising above the surface of the sample;

c) an oscillator for oscillating the spring; and d) a displacement detector for detecting the displacement of the spring.

The apparatus is used as follows. First a fluid sample is put into the vessel and the spring is set standing in the vessel with the top rising above the surface of the sample. Then the spring is oscillated by the oscillator with a constant amplitude of force, while the displacement of the spring is detected. As the fluid sample gradually solidifies, the amplitude of the oscillating displacement becomes smaller, which can be recorded with respect to the time, temperature, or other parameters that may cause the state change.

The apparatus may further include a heater or cooler for heating or cooling the sample while the sample is oscillated.

Since the thermomechanical analyzer of the present invention analyzes the change of the state dynamically, it is suited for measuring conditions of the state change of adhesives which require measurements under an application of force.

DETAILED DESCRIPTION OF A PREFERRED EMBODIMENT

A dynamic thermomechanical analyzer for measuring the solidifying temperature of an adhesive sample is now described as an embodiment of the invention. The adhesive sample analyzed here is initially fluid, but becomes viscous as it is heated, and finally solidifies. The dynamic thermomechanical analyzer of the embodiment measures the temperatures at which such changes of state occur.

Figure 1:
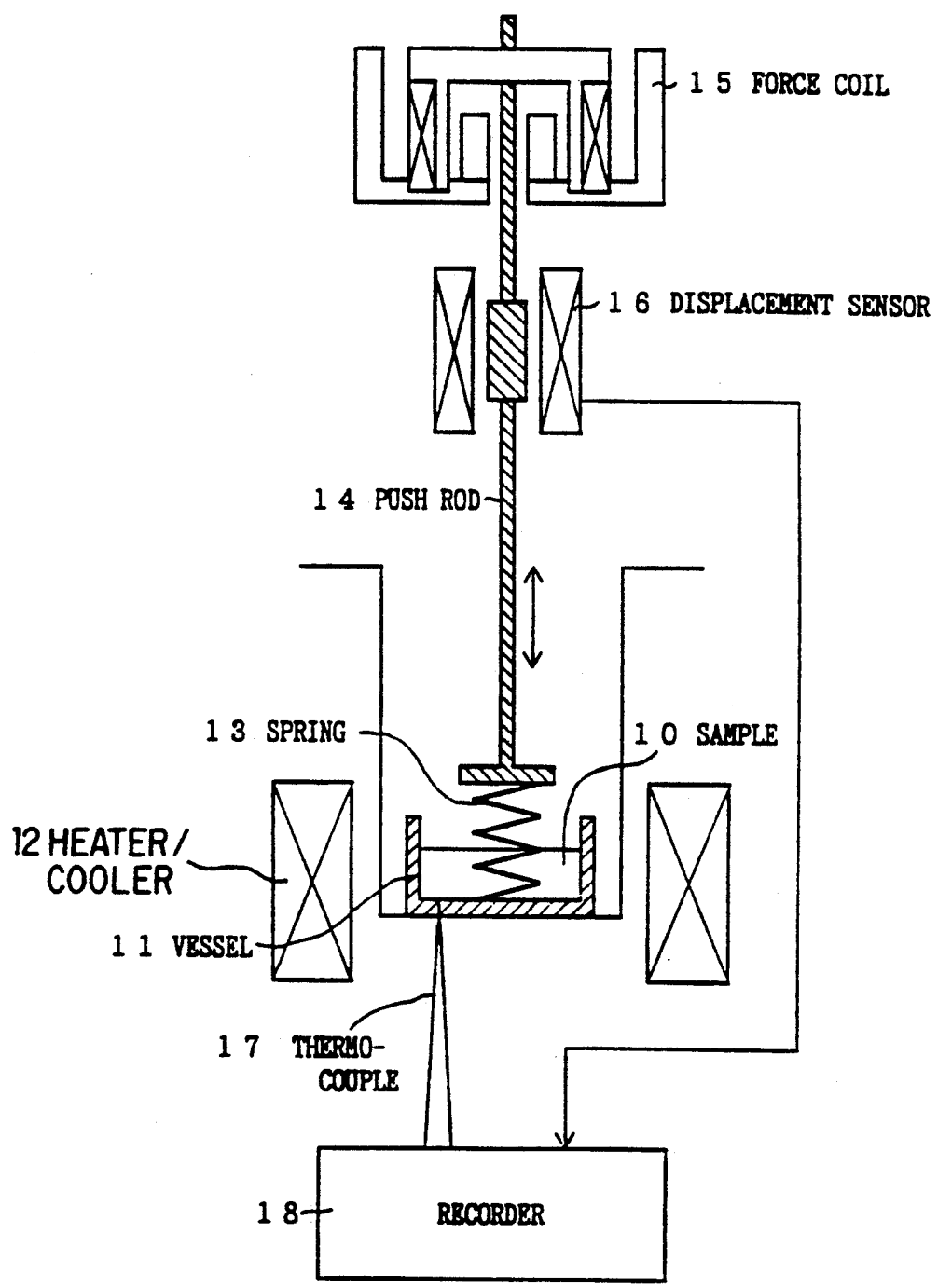
FIG. 1 is a vertical cross-sectional view of a dynamic thermomechanical analyzer as an embodiment of the present invention.
Figure 3:
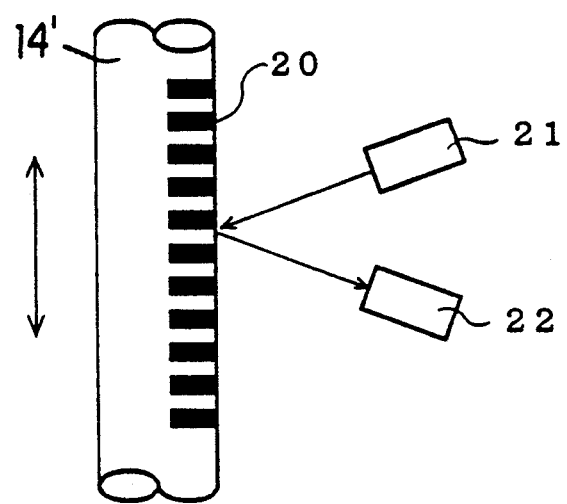
FIG. 3 is a side view of a photosensor for detecting the displacement of the push rod.

The dynamic thermomechanical analyzer includes, as shown in FIG. 1: a sample vessel 11; a helical spring 13 placed standing in the sample vessel 10; a push rod 14 having a flat bottom abutting on the helical spring 13; a heater 12 surrounding the sample vessel 10; a force coil 15 provided at the top of the push rod 14; a displacement sensor 16 provided around the push rod 14; and a recorder 18. The force coil 15 is a solenoid for oscillating the push rod 14 vertically with the electromagnetic force. The displacement sensor 16 is a differential transformer using a bulge of the push rod as the moving core, and measures the vertical displacement of the push rod 14. As shown in FIG. 3, a gradation 20 printed on the surface of the push rod 14', a light source 21, and a photosensor 22 can be used instead of the differential transformer as the displacement sensor 16. Any other kind of displacement sensor can be used, of course. The displacement sensor 16 can be placed above the force coil 15, instead of below as shown in FIG. 1. A temperature sensor 17, thermo-couple in this embodiment, is provided in the sample vessel 11. The displacement sensor 16 and the temperature sensor 17 send signals to the recorder 18.

Figure 2A:
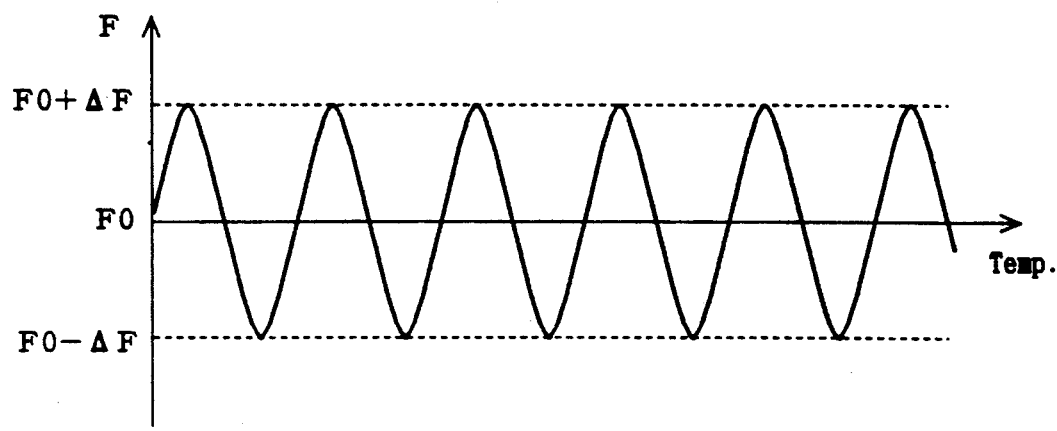
FIG. 2A is a graph showing the change in the force applied to the spring of the dynamic thermomechanical analyzer of the embodiment.

When an adhesive sample is measured, the initially fluid adhesive sample 10 is put into the sample vessel 11 to about the half height of the helical spring 13. Then the push rod 14 is oscillated (reciprocated) by the force coil 15, while the adhesive sample 10 is gradually heated by the heater 12 at a preset rate. Here the mean value $F_0$ and the amplitude $\Delta F$ of the oscillating force F of the force coil 15 is kept constant throughout the test, as shown in FIG. 2A.

Figure 2B:
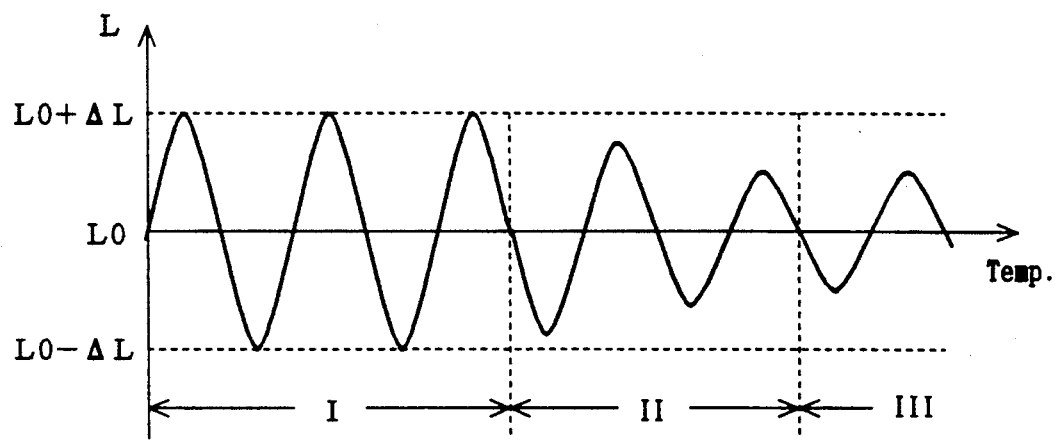
FIG. 2B is a graph showing the change in the displacement of the push rod of the dynamic thermomechanical analyzer of the embodiment.
Figure 2C:
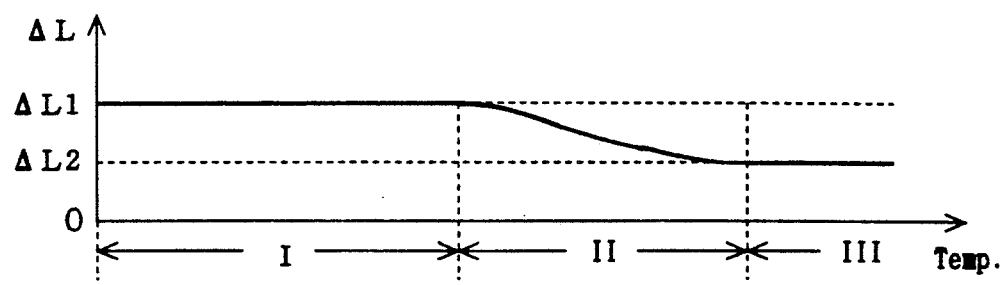
FIG. 2C is a graph showing the change in the amplitude of the displacement.

The displacement L of the push rod 14 measured by the displacement sensor 16 is shown in FIG. 2B. At first in the region I, that is, while the temperature of the adhesive sample 10 is not high, the adhesive sample 10 has the same fluidity as the initial state and the amplitude $\Delta L$ of the displacement of the push rod 14 is constant at $\Delta L_1$. When the temperature of the sample 10 exceeds a certain point, the state of the sample 10 enters into a new region II in which the adhesive sample 10 gradually gains viscosity. As the sample 10 becomes viscous, the movement of the lower half of the spring 13 is hampered and the effective length of the helical spring 13 becomes shorter. This increases the spring constant of the spring 13 and the amplitude $\Delta L$ of the oscillation of the push rod 14 gradually decreases. When the adhesive sample 10 completely solidifies, the helical spring 13 is effective only at its upper half rising above the surface of the solidified sample 10, and the amplitude $\Delta L$ of the oscillation of the push rod 14 becomes constant at a small value $\Delta L_2$ (region III). The change in the amplitude $\Delta L$ of the oscillation of the push rod 14 is recorded with respect to the temperature of the sample 10 (which is measured by the thermo-couple 17) by the recorder 18, as shown in FIG. 2C. The graph of FIG. 2C clearly shows the changing characteristic of the adhesive sample 10 as it is heated. It is noted here that the graph of FIG. 2B is simplified for the convenience of explanation, but the mean position of the oscillation of the push rod 14 may change as the movement of the lower half of the spring 13 is restricted.

The amplitude $\Delta F$ of the oscillating force F of the force coil 15 is kept constant in the forgoing description of the embodiment for simplicity. But the analysis of the state change is possible even if the amplitude is changed after the change in the amplitude $\Delta L$ of the push rod 14 is normalized by the change in the amplitude $\Delta F$ of the oscillating force F.

When a sample that is fluid at normal temperature and solidifies as the temperature decreases is tested, the heater 12 is replaced by a cooler. A thermodynamic refrigerator or a simple container of coolant (such as dry ice or liquid nitrogen) can be used as the cooler. When a sample that solidifies not by the change in temperature but by the passage of time is tested, no such apparatus is needed. A mixture type (two ingredient-type) adhesive or a chemical agent that solidifies as it is oxidized or as it absorbs environment gas may be tested without heater or refrigerator.

What is claimed is:

1. An apparatus for analyzing a change of the state of a sample from a fluid state to a solid state, the apparatus comprising:
   a) a vessel in which the sample is set;
   b) a spring standing in the vessel, the top of the spring rising above the surface of the sample;
   c) an oscillator means for oscillating the spring including a push rod placed on the top of the spring and a solenoid means for driving the push rod; and
   d) a displacement detector coacting with a portion of said push rod for detecting the displacement of the spring.

2. The apparatus according to claim 1, where the oscillator means oscillates the spring with a constant amplitude of force.

3. The apparatus according to claim 2, wherein the apparatus further comprises a heater for heating the sample.

4. The apparatus according to claim 3, where the apparatus further comprises a temperature sensor for sensing the temperature of the sample and a recorder for recording the relationship between the temperature of the sample and the displacement.

5. The apparatus according to claim 3, where the spring is a helical spring.

6. The apparatus according to claim 5, where the displacement detector includes a graduation on the push rod and a photosensor for sensing the graduation.

7. The apparatus according to claim 5, where the displacement detector is a differential transformer using the push rod as the core rod.

8. The apparatus according to claim 2, where the apparatus further comprises a recorder for recording the relationship between the testing time and the displacement.

9. The apparatus according to claim 2, where the apparatus further comprises a cooler for cooling the sample.

10. The apparatus according to claim 9, where the apparatus further comprises a temperature sensor for sensing the sample and a recorder for recording the relationship between the temperature of the sample and the displacement.

* * * * *